United States Patent [19]

Moore

[11] Patent Number: 5,756,342
[45] Date of Patent: May 26, 1998

US005756342A

[54] BCRF1 ANTAGONISTS FOR TREATING EPSTEIN-BARR VIRUS INFECTIONS

[75] Inventor: Kevin W. Moore, Palto Alto, Calif.

[73] Assignee: Schering Corporation, Kenilworth, N.J.

[21] Appl. No.: 461,778

[22] Filed: Jun. 5, 1995

Related U.S. Application Data

[63] Continuation of Ser. No. 382,932, Feb. 2, 1995, which is a continuation of Ser. No. 152,936, Nov. 15, 1993, abandoned, which is a continuation of Ser. No. 993,504, Dec. 16, 1992, abandoned, which is a continuation of Ser. No. 859,618, Mar. 23, 1992, abandoned, which is a continuation of Ser. No. 498,985, Mar. 26, 1990, abandoned.

[51] Int. Cl.$^6$ .................... C12N 5/12; C07K 16/08; A61K 39/395

[52] U.S. Cl. .................... 435/240.27; 530/387.3; 530/388.23; 530/388.3; 530/388.85; 530/389.2; 435/240.2; 424/141.1; 424/158.1

[58] Field of Search .................... 530/387.3, 388.23, 530/388.73, 389.2; 435/240.27; 424/141.1, 158.1

[56] References Cited

U.S. PATENT DOCUMENTS 5,231,012 7/1993 Mosmann et al. .................... 435/69.52

FOREIGN PATENT DOCUMENTS 0 179 254 3/1986 European Pat. Off. .

OTHER PUBLICATIONS

Seaver, Genetic Engineering News 14:10.21 1994.
Harns et al., Tibtech 11:42–44, 1993.
Casali et al., Science 234:476–479, 1986.
Baer et al., "DNA seuence and expression of the b95–8 Epstein–Barr virus genome," *Nature* 310:207–211 (Jul. 1984).
Bean et al., "Interleukin 10 protects mice against *staphylococcal enterotoxin*B–induced lethal shock," *Infection and Immuity* 61(10):4937–4939 (1993).
de Waal Malefyt et al., "Interleukin 10 (IL–10) inhibits cytokine synthesis by human monocytes: An autoregulatory role of IL–10 produced by monocytes," *J. Exp. Med.* 174:1209–1220 (1991).
Fiorentino et al., "Two types of mouse T helper cell IV. Th2 clones secrete a factor that inhibits cytokine production by Th1 clones," *Journal of Experimental Medicine* 170:2081–2095 (1989).
Fiorentino et al., "IL–10 inhibits cytokine production by activated macrophages," *The Journal of Immunology* 147(11):3815–3822 (1991).
Go et al., "Interleukin 10, a novel B cell stimulatory factor: Unresponsiveness of X chromosome–linked immunodeficiency B cells," *Journal of Experimental Medicine* 172(6):1625–1631 (1990).
Hirsch, "Herpesvirus infections," *Scientific American Medicine* 2(Chapter XXVI):1–11 (Oct. 1992).

Horowitz et al., "Autocrine growth inhibition of a cloned line of helper T cells," *Proc. Natl. Acad. Sci. USA* 83:1886–1890 (1986).
Howard et al., "Interleukin 10 protects mice from lethal endotoxemia," *J. Exp. Med.* 177:1205–1211 (1993).
Hsu et al., "differential effects of IL–4 and IL–10 on IL–2 induced IFN–γ synthesis and lumphokine–activated killer activity," *J. of Immunol.* 6:663–663 (1992).
Hsu, "Expression of interleukin–10 activity by Epstein–Barr virus protein BCRF1," *Science* 250:830–832 (Nov. 1990).
Hudson et al., "The short unique region of the B95–8 Epstein–Barr virus genome," *Virology* 147:81–98 (1985).
International Search Report from corresponding application (Jul. 1991).
Joakim Dillner et al., "The Epstein–Barr virus proteins," *Advances in Cancer Research* 50:95–158 (1988).
Köhler et al., "Continuous cultures of fused cells secreting antibody of predefined specificity," *Nature* 256:495–497 (Aug. 1975).
Marchant et al., "Interleukin–10 controls interferon–γ and tumor necrosis factor production during experimental endotoxemia," *Eur. J. Immunol.* 24:1167–1171 (1994).
McDevitt, "The molecular basis of autoimmunity," *Clinical Research* 34:163–175 (1985).
Moore et al., "Homology of cytokine synthesis inhibitory factor (IL–10) to the Epstein–Barr virus gene BCRFI," *Science* 248:1230–1234 (Jun. 1990).
Schooley et al., "Epstein–Barr virus (infectious mononucleosis)," *Principles and Practice of Infectious Disease*, second ed., John Wiley & Sons, Chapter 126, pp. 971–979 (1985).
Swaminathan et al., "Epstein–Barr virus recombinants with specifically mutated BCRF1 genes," *Journal of Virology* 67(2):7406–7413 (1993).
Thorley–Lawson, "Immunological responses to Epstein–Barr virus infection and the pathogenesis of EBV–induced diseases," *Biochimica et Biophysica Acta*, 948:263–286 (1988).
Tosato, "The Epstein–Barr virus and the immune system," *Advances in Cancer Research*, 49:75–125 (1987).
Vieiera et al., "Isolation and expression of human cytokine synthesis inhibitory factor cDNA clones: Homology to Epstein–Barr virus open reading frame BCRF1," *Proc. Natl. Acad. Sci. USA* 88:1172–1176 (1991).
von Heijne, "A new method for predicting signal sequence cleavage sites," *Nucleic Acids Research* 14(11):4683–4690 (1986).

(List continued on next page.)

*Primary Examiner*—Lila Feisee
*Assistant Examiner*—Nancy A. Johnson
*Attorney, Agent, or Firm*—Stephen C. Macevicz; Karen B. Dow; Randolph T. Apple

[57] ABSTRACT

A method of treating EBV infections is provided. The method comprises administering an effective amount of an monoclonal antibody antagonist to the EBV protein, BCRF1. Preferably, the antagonist is a blocking monoclonal antibody specific for BCRF1, or a fragment or binding composition derived therefrom.

12 Claims, 2 Drawing Sheets

OTHER PUBLICATIONS

Waldmann, "Monoclonal antibodies in diagnosis and therapy," *Science*, 252:1657–1662 (Jun. 1991).

Albert Zlotnik, et al., "Effects of IL–10 in Lipopolysaccharide– and Superantigen–Induced Lethal Shock in Vivo", *Molecular Biology Intelligence Unit – Interleukin 10*, Chapter 13, pp. 121–126 (1995).

BCRF1 ANTAGONISTS FOR TREATING EPSTEIN-BARR VIRUS INFECTIONS

This is a Continuation of application Ser. No. 08/382,932, filed Feb. 2, 1995, which is a FWC of Ser. No. 08/152,936, filed Nov. 15, 1993, now abandoned, which is a FWC of Ser. No. 07/993,504, filed Dec. 16, 1992, now abandoned, which is a FWC of Ser. No. 07/859,618, filed Mar. 23, 1992, now abandoned, which is a FWC of Ser. No. 07/498,985, filed Mar. 26, 1990, now abandoned.

FIELD OF THE INVENTION

The invention relates to a method of treating Epstein-Barr virus (EBV) infections by administering antagonists to the EBV protein, BCRF1.

BACKGROUND

Epstein-Barr virus (EBV) is an ubiquitous human herpes virus that was first discovered in association with the African (endemic or e) form of Burkitt's lymphoma. Subsequently the virus was also found associated with nasopharyngeal carcinoma and was shown to be the causative agent of infectious mononucleosis. Infection usually occurs during early childhood, generally resulting in a subclinical manifestation, occasionally with mild symptoms. Infection during adolescence or adulthood, however, can give rise to infectious mononucleosis characterized by the presence of sore throat, fever and lymphadenopathy. Most cases of infectious mononucleosis resolve in one to three weeks, although malaise and fatigue occasionally persist for several weeks to months. Complications that occur occasionally include extreme tonsillar enlargement, thrombocytopenia, splenic rupture, jaundice, and encephalitis. Also, in immunocompromised patients, such as transplant recipients and AIDS patients, EBV infections can lead to B cell lymphoproliferative disorders. College and military populations experience the highest morbidity from infectious mononucleosis, e.g. accounting for 5 percent of all hospitalizations of University of Wisconsin students, and ranking fourth as the cause of days lost due to illness in army personnel. Thorley-Lawson, Biochimica et Biophsica Acta, Vol. 948, pgs 263–286 (1988); Schooley et al, chapter 126 in Mandell et al, eds. Principles and Practice of Infectious Diseases, 2nd Ed. (John Wiley & Sons, New York, 1985).

The availability of agents to treat EBV infected individuals could have a significant clinical impact, particularly in the treatment of immunocompromised individuals.

SUMMARY OF THE INVENTION

The invention is a method of treating EBV infections by administering an effective amount of an antagonist to the EBV protein, BCRF1. Preferably, the antagonists to BCRF1 are monoclonal antibodies, or binding compositions derived therefrom by standard techniques.

DETAILED DESCRIPTION OF THE INVENTION

Figure 1:
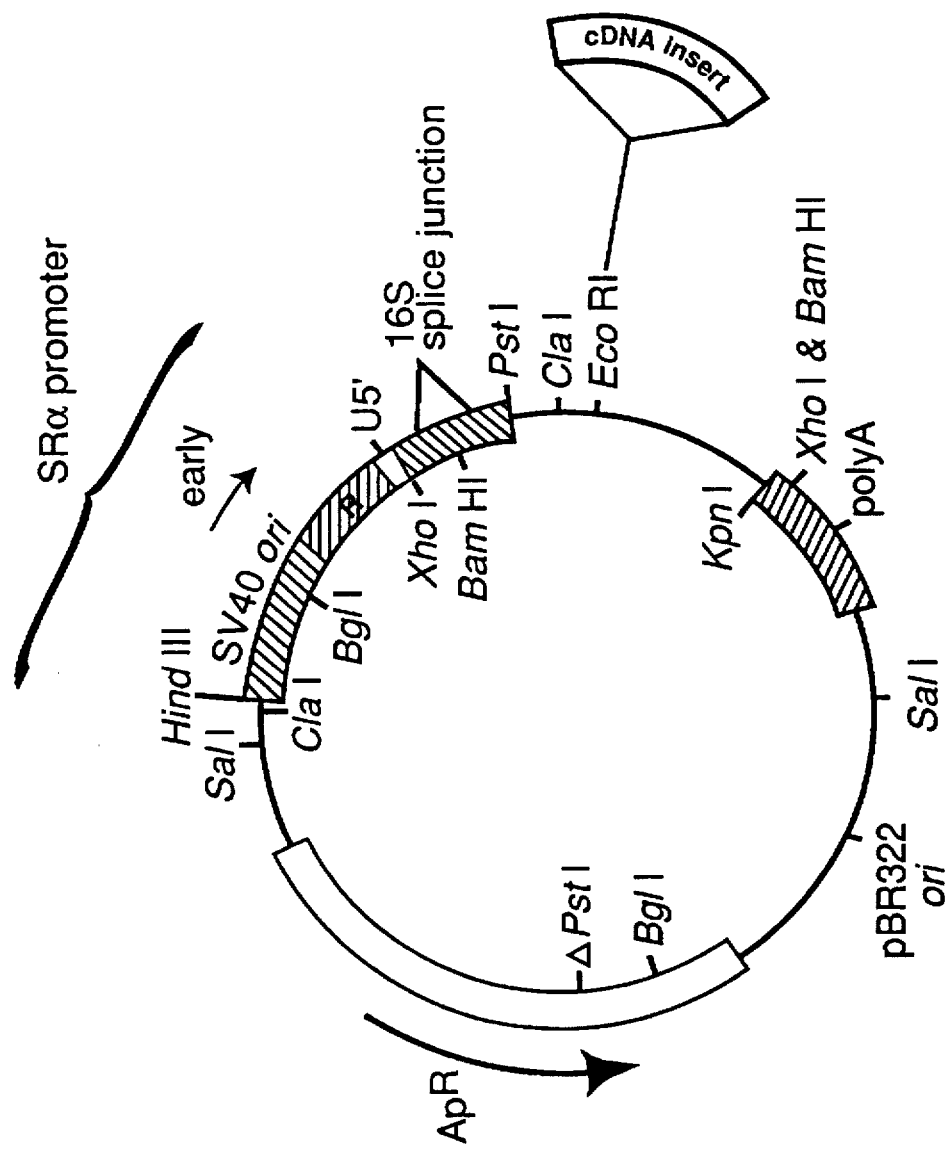
FIG. 1 is a diagrammatic illustration of a mammalian expression vector useful in the production of BCRF1.
Figure 2:
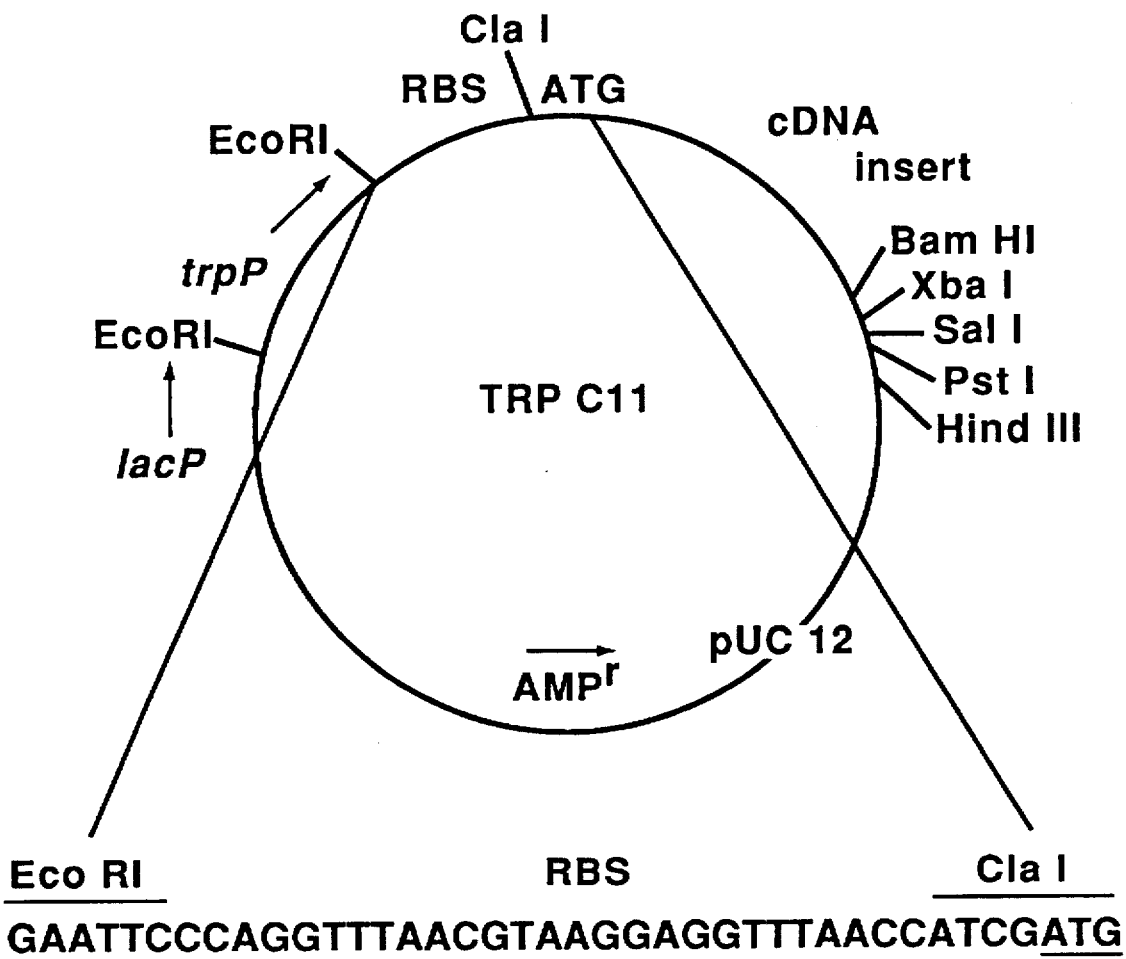
FIG. 2 is a diagrammatic illustration of a bacterial expression vector useful in the production of BCRF1.

The invention is based in part on the discovery that BCRF1 suppresses the production of interferon-γ (IFN-γ), a cytokine necessary for cell-mediated defenses against viral infections. It is believed that BCRF1 is produced by EBV to enhance its survival in its host. The method of the invention comprises administering to an individual an effective, or disease-ameliorating, amount of an antagonist to BCRF1.

Preferably, antagonists of the invention are derived from antibodies specific for BCRF1. More preferably, the antagonists of the invention comprise fragments or binding compositions specific for BCRF1. Antibodies comprise an assembly of polypeptide chains linked together by disulfide bridges. Two major polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three different constant regions, and light chains comprise a single variable region (different from that of the heavy chain) and a single constant region (different from those of the heavy chain). The variable regions of the heavy chain and light chain are responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

As used herein the term "monoclonal antibody" refers to homogeneous populations of immunoglobulins which are capable of specifically binding to BCRF1.

As used herein the term "binding composition" means a composition comprising two polypeptide chains (1) which, when operationally associated, assume a conformation having high binding affinity for BCRF1, and (2) which are derived from a hybridoma producing monoclonal antibodies specific for BCRF1. The term "operationally associated" is meant to indicate that the two polypeptide chains can be positioned relative to one another for binding by a variety of means, including by association in a native antibody fragment, such as Fab or Fv, or by way of genetically engineered cysteine-containing peptide linkers at the carboxyl termini. Normally, the two polypeptide chains correspond to the light chain variable region and heavy chain variable region of a monoclonal antibody specific for BCRF1. Preferably, antagonists of the invention are derived from monoclonal antibodies specific for BCRF1. Monoclonal antibodies capable of blocking, or neutralizing, BCRF1 are selected by their ability to inhibit BCRF1-induced suppression of interferon-γ production. Such assays require a cell line or cell population that synthesizes IFN-γ. Conveniently, peripheral blood lymphocytes (PBLs) that have been stimulated with a mitogen such as phytohemagglutinin (PHA) can serve as such a cell population. Roughly, the assay works as follows: The PHA-stimulated PBLs are divided into three equal portions. To the first portion, BCRF1 is added. To the second portion, BCRF1 and the putative antagonist is added. The third portion serves as a control. After several days the supernatants of cultures are tested for IFN-γ. This is conveniently done with a standard ELISA assay using commercially available monoclonal and polyclonal antibodies for IFN-γ, e.g. Genzyme, Inc. (Boston, Mass.). Alternatively, the readout of the assay can be the amount of IFN-γ mRNA transcribed, for example, as measured by RNA blotting, PCR, or like methodology. PBLs are obtained using standard techniques, e.g. Mishell et al. eds., *Selected Methods in Cellular Immunology* (Freeman, New York, 1980).

Hybridomas of the invention are produced by well known techniques. Usually, the process involves the fusion of an immortalizing cell line with a B-lymphocyte which produces the desired antibody. Alternatively, non-fusion techniques for generating an immortal antibody producing cell lines are possible, and come within the purview of the present invention, e.g. virally induced transformation: Casali et al., "Human Monoclonals from Antigen-Specific Selection of B Lymphocytes and Transformation by EBV," Science, Vol. 234, pgs. 476–479 (1986). Immortalizing cell lines are usually transformed mammalian cells, particularly myeloma cells of rodent, bovine, and human origin, e.g. U.S. Pat. Nos. 4,693,975 and 4,720,459. Most frequently, rat or mouse myeloma cell lines are employed as a matter of convenience and availability. Techniques for obtaining the appropriate lymphocytes from mammals injected with the target antigen are well known. Generally, either peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody producing cells before these are harvested for fusion with the immortalizing cell line. Preferably, the mammalian source of antibody-producing B cells is mouse, rat, rabbit, or human. Techniques for fusion are also well known in the art, and in general, involve mixing the cells with a fusing agent, such as polyethylene glycol. Hybridomas are selected by standard procedures, such as HAT selection. From among these hybridomas, those secreting the desired antibody, i.e. specific for BCRF1, are selected by assaying their culture medium by standard immunoassays, such as Western blotting, ELISA, RIA, BCRF1 neutralizing capability, or the like. Antibodies are recovered from the medium using standard protein purification techniques, e.g. Tijssen, *Practice and Theory of Enzyme Immunoassays* (Elsevier, Amsterdam, 1985). Many references are available for guidance in applying any of the above techniques, e.g. Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982); and the like. Hybridomas producing monoclonal antibodies specific for BCRF1 are then subjected to a second screen using the IFN-γ-suppression assay described above to select ones capable of blocking, or neutralizing, the biological activity of BCRF1.

The use and generation of fragments of antibodies is also well known, e.g. Fab fragments: Tijssen, *Practice and Theory of Enzyme Immunoassays* (Elsevier, Amsterdam, 1985); and Fv fragments: Hochman et al. *Biochemistry*, Vol. 12, pgs. 1130–1135 (1973), Sharon et al., *Biochemistry*, Vol. 15, pgs. 1591–1594 (1976) and Ehrlich et al., U.S. Pat. No. 4,355,023; and antibody half molecules: Auditore-Hargreaves, U.S. Pat. No. 4,470,925.

Hybridomas and monoclonal antibodies of the invention are produced against either glycosylated or unglycosylated versions of recombinantly produced mature BCRF1 as immunogens. Generally, unglycosylated versions of BCRF1 are produced in *E. coli*, and glycosylated versions are produced in mammalian cell hosts, e.g. CV1 or COS monkey cells, mouse L cells, or the like. Recombinantly produced mature BCRF1 is produced by introducing an expression vector into a host cell using standard protocols, e.g. Maniatis et al., *Molecular Cloning: A Laboratory Manual* (Cold Spring Harbor Laboratory, New York, 1982); Okayama and Berg, *Mol. Cell. Biol.*, Vol. 2, pgs. 161–170 (1982) and Vol. 3, pgs. 280–289 (1983); Takebe et al. *Mol. Cell. Biol.*, Vol. 8, pgs. 466–472 (1988); U.S. Pat. No. 4,599,308; U.S. Pat. No. 4,675,285; Kaufman et al., *Mol. Cell. Biol.*, Vol. 2, pgs. 1304–1319 (1982); or the like. Construction of bacterial or mammalian expression vectors are well known in the art, once the nucleotide sequence encoding a desired protein is known or otherwise available, e.g. DeBoer in U.S. Pat. No. 4,551,433 discloses promoters for use in bacterial expression vectors; Goeddel et al., in U.S. Pat. No. 4,601,980, and Riggs, in U.S. Pat. No. 4,431,739 disclose the production of mammalian proteins by *E. coli* expression systems; and Riggs (cited above), Ferretti et al., *Proc. Natl. Acad. Sci.*, Vol. 83, pgs. 599–603 (1986), Sproat et al., *Nucleic Acids Research*, Vol.13, pgs. 2959–2977 (1985), and Mullenbach et al., *J. Biol. Chem.*, Vol. 261, pgs. 719–722 (1986) disclose how to construct synthetic genes for expression in bacteria. Accordingly, these references are incorporated by reference. BCRF1 may also be produced by transiently transfecting COS 7 cells with pBCRF1(SRα), a plasmid deposited with the American Type Culture Collection (Rockville, Md.) under accession number 68193 as part of this disclosure. FIG. 1 is a restriction map of pBCRF1(SRα).

The largest open reading frame of the BCRF1 cDNA is defined by the following sequence of amino acids:

Met — Glu — Arg — Arg — Leu — Val — Val — Thr — Leu — Gln — Cys —
Leu — Val — Leu — Leu — Tyr — Leu — Ala — Pro — Glu — Cys — Gly —
Gly — Thr — Asp — Gln — Cys — Asp — Ala — Phe — Pro — Gln — Met —
Leu — Arg — Asp — Leu — Arg — Asp — Ala — Phe — Ser — Arg — Val —
Lys — Thr — Phe — Phe — Gln — Thr — Lys — Asn — Glu — Val — Asp —
Asn — Leu — Leu — Leu — Lys — Glu — Ser — Leu — Leu — Glu — Asp —
Phe — Lys — Gly — Tyr — leu — Gly — Cys — Gln — Ala — Leu — Ser —
Glu — Met — Ile — Gln — phe — Tyr — Leu — Glu — Glu — Val — Met —
Pro — Gln — Ala — Glu — Asn — Glna — Asp — Pro — Glu — Ala — Lys —
Asp — His — Val — Asn — Ser — Leu — Gly — Glu — Asn — Leu — Lys —
Thr — Leu — Arg — Leu — Arg — Leu — Arg — Arg — Cys — His — Arg —
Phe — Leu — Pro — Cys — Glu — Asn — Lys — Ser — Lys — Ala — Val —
Glu — Gln — Ile — Lys — Asn — Ala — Phe — Asn — Lys — Leu — Gln —
Glu — Lys — Gly — Ile — Tyr — Lys — Ala — Met — Ser — Glu — Phe —
Asp — Ile — Phe — Ile — Asn — Tyr — Ile — Glu — Ala — Tyr — Met —
Thr — Ile — Lys — Ala — Arg A description of the EBV genome is given by Baer et al. *Nature*, Vol. 310, pgs. 207–211 (1984), and the nucleotide sequence of the BCRF1 cDNA is available in GenBank release 26.

When BCRF1 is expressed in soluble form, for example as a secreted product of transformed yeast or mammalian cells, they can be purified according to standard procedures of the art, including steps of ammonium sulfate precipitation, ion exchange chromatography, gel filtration, electrophoresis, affinity chromatography, and/or the like, e.g. "Enzyme Purification and Related Techniques," *Methods in Enzymology*, 22:233–577 (1977), and Scopes, *Protein Purification: Principles and Practice* (Springer-Verlag, New York, 1982) provide guidance in such purifications. Likewise, when BCRF1 is expressed in insoluble form, for example as aggregates, inclusion bodies or the like, they can be purified by standard procedures in the art, including separating the inclusion bodies from disrupted host cells by centrifugation, solubilizing the inclusion bodies with chaotropic and reducing agents, diluting the solubilized mixture, and lowering the concentration of chaotropic agent and reducing agent so that the polypeptide takes on a biologically active conformation. The latter procedures are disclosed in the following references, which are incorporated by reference: Winkler et al., Biochemistry, 25: 4041–4045 (1986); Winkler et al., Biotechnology, 3: 992–998 (1985); Koths et al., U.S. Pat. No. 4,569,790; and European patent applications 86306917.5 and 86306353.3.

Antibodies and antibody fragments characteristic of hybridomas of the invention can also be produced by recombinant means by extracting messenger RNA, constructing a cDNA library, and selecting clones which encode segments of the antibody molecule, e.g. Wall et al., Nucleic Acids Research, Vol. 5, pgs. 3113–3128 (1978); Zakut et al., Nucleic Acids Research, Vol. 8, pgs. 3591–3601 (1980); Cabilly et al., Proc. Natl. Acad. Sci., Vol. 81, pgs. 3273–3277 (1984); Boss et al., Nucleic Acids Research, Vol. 12, pgs. 3791–3806 (1984); Amster et al., Nucleic Acids Research, Vol. 8, pgs. 2055–2065 (1980); Moore et al., U.S. Pat. No. 4,642,334; Skerra et al., Science, Vol. 240, pgs. 1038–1041(1988); Huse et al., Science, Vol. 246, pgs. 1275–1281 (1989); Better et al., Science, Vol. 240, pgs. 1041–1043 (1988); and Riechmann et al., Nature, Vol. 332, pgs. 323–327 (1988). In particular, such techniques can be used to produce interspecific monoclonal antibodies, wherein the binding region of one species is combined with non-binding region of the antibody of another species to reduce immunogenicity, e.g. Liu et al., Proc. Natl. Acad. Sci., Vol. 84, pgs. 3439–3443 (1987).

Antagonists of the invention are administered as a pharmaceutical composition. Such compositions contain a therapeutic amount of at least one of the monoclonal antibodies of the invention, or fragments thereof, in a pharmaceutical carrier. A pharmaceutical carrier can be any compatible, non-toxic substance suitable for delivering the compositions of the invention to a patient. Sterile water, alcohol, fats, waxes, and inert solids may be included in a carrier. Pharmaceutically accepted adjuvants (buffering agents, dispersing agents) may also be incorporated into the pharmaceutical composition. Generally, compositions useful for parenteral administration of such drugs are well known, e.g. Remington's Pharmaceutical Science, 15th Ed. (Mack Publishing Company, Easton, Pa. 1980). Alternatively, compositions of the invention may be introduced into a patient's body by implantable or injectable drug delivery system, e.g. Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); Johnson et al, eds. Drug Delivery Systems: Fundamentals and Techniques (Ellis Horwood, Ltd., London, 1987); U.S. Pat. No. 3,773,919; U.S. Pat. No. 3,270,960; and the like.

When the antagonists of the inventions are derived from antibodies, they are normally administered parentally, preferably intravenously. Since such protein or peptide antagonists may be immunogenic they are preferably administered slowly, either by a conventional IV administration set or from a subcutaneous depot, e.g. as taught by Tomasi et al, U.S. Pat. No. 4,732,863. When administered parenterally the antibodies or fragments will be formulated in a unit dosage injectable form (solution, suspension, emulsion) in association with a pharmaceutically acceptable parenteral vehicle. Such vehicles are inherently nontoxic and nontherapeutic. Examples of such vehicles are normal saline, Ringer's solution, dextrose solution, and Hank's solution. Nonaqueous vehicles such as fixed oils and ethyl oleate may also be used. A preferred vehicle is 5% dextrose/saline. The vehicle may contain minor amounts of additives such as substances that enhance isotonicity and chemical stability, e.g., buffers and preservatives. The antibody is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml.

Selecting an administration regimen for an antagonist depends on several factors, including the serum turnover rate of the antagonist, the serum level of BCRF1, the immunogenicity of the antagonist, the accessibility of the target BCRF1, and the like. Preferably, an administration regimen maximizes the amount of antagonist delivered to the patient consistent with an acceptable level of side effects. Accordingly, the amount of antagonist delivered depends in part on the particular antagonist and the severity of the condition being treated. Guidance in selecting appropriate doses is found in the literature on therapeutic uses of antibodies, e.g. Bach et al., chapter 22, in Ferrone et al., eds., Handbook of Monoclonal Antibodies (Noges Publications, Park Ridge, N.J., 1985); and Russell, pgs. 303–357, and Smith et al., pgs. 365–389, in Haber et al., eds. Antibodies in Human Diagnosis and Therapy (Raven Press, New York, 1977). Preferably, whenever the antagonist comprises monoclonal antibodies or Fab-sized fragments thereof (including binding compositions), the dose is in the range of about 1–20 mg/kg per day. More preferably the dose is in the range of about 1–10 mg/kg per day.

The following examples serve to illustrate aspects of the present invention. Selection of vectors, hosts, fusion partners as well as concentration of reagents, temperatures, and the values of other variable parameters are only to exemplify the invention and are not to be considered as limitations thereof.

EXAMPLE 1

Expression of BCRF1 in COS 7 Monkey cells

A gene encoding the open reading frame for BCRF1 was amplified by polymerase chain reaction using primers that allowed later insertion of the amplified fragment into an Eco RI-digested pcD(SRα) vector (FIG. 1). The coding strand of the inserted fragment is shown below (the open reading frame being given in capital letters).

```
a a t t c ATGGA   GCGAAGGTTA  GTGGTCACTC  TGCAGTGCCT  GGTGCTGCTT

TACCTGGCAC       CTGAGTGTGG  AGGTACAGAC  CAATGTGACA  ATTTTCCCCA

GACCTAAGAG       ATGCCTTCAG  TCGTGTTAAA  ACCTTTTTCC  AGACAAAGGA

CGAGGTAGAT       AACCTTTTGC  TCAAGGAGTC  TCTGCTAGAG  GACTTTAAGG

ATGCCAGGCC       CTGTCAGAAA  TGATCCAATT  CTACCTGGAG  GAAGTCATGC

CACAGGCTGA       AACCAGGAC   CCTGAAGCCA  AAGACCATGT  CAATTCTTTG
```

```
                                           -continued
GGTGAAAATC  TAAAGACCCT  ACGGCTCCGC  CTGCGCAGGT  GCCACAGGTT

CCTGCCGTGT  GAGAACAAGA  GTAAAGCTGT  GGAACAGATA  AAAAATGCCT

TTAACAAGCT  GCAGGAAAAA  GGAATTTACA  AAGCCATGAG  TGAATTTGAC

ATTTTTATTA  ACTACATAGA  AGCATACATG  ACAATTAAAG  CCAGGTGAg
```

Clones carrying the insert in the proper orientation were identified by expression of BCRF1 and/or the electrophoretic pattern of restriction digests. One such vector carrying the BCRF1 gene was designated pBCRF1(SRα) and was deposited with the ATCC under accession number 68193. pBCRF1(SRα) was amplified in *E. coli* MC1061, isolated by standard techniques, and used to transfect COS 7 monkey cells as follows: One day prior to transfection, approximately $1.5 \times 10^6$ COS 7 monkey cells were seeded onto individual 100 mm plates in Dulbecco's modified Eagle medium (DME) containing 5% fetal calf serum (FCS) and 2 mM glutamine. To perform the transfection, COS 7 cells were removed from the dishes by incubation with trypsin, washed twice in serum-free DME, and suspended to $10^7$ cells/ml in serum-free DME. A 0.75 ml aliquot was mixed with 20 μg DNA and transferred to a sterile 0.4 cm electroporation cuvette. After 10 minutes, the cells were pulsed at 200 volts, 960 μF in a BioRad Gene Pulser unit. After another 10 minutes, the cells were removed from the cuvette and added to 20 ml of DME containing 5% FCS, 2 mM glutamine, penicillin, streptomycin, and gentamycin. The mixture was aliquoted to four 100 mm tissue culture dishes. After 12–24 hours at 37° C., 5% $CO_2$, the medium was replaced with similar medium containing only 1% FCS and the incubation continued for an additional 72 hours at 37° C., 5% $CO_2$, after which the medium was collected and assayed for its ability to inhibit IFN-γ synthesis.

10 ml aliquots of freshly isolated PBLs (about $2 \times 10^6$ cells/ml) were incubated at 37° C. with PHA (100 ng/ml) in medium consisting of (i) 90% DME supplemented with 5% FCS and 2 mM glutamine, and (ii) 10% supernatant from COS 7 cells previously transfected with pBCRF1(SRα). After 24 hours the cells and supernatants were harvested to assay for the presence of either IFN-γ mRNA or IFN-γ protein, respectively. Controls were treated identically, except that the 10% supernatant was from COS 7 cultures previously transfected with a plasmid carrying an unrelated cDNA insert. The BCRF1-treated samples exhibited about a 50% inhibition of IFN-γ synthesis relative to the controls.

EXAMPLE 2

Expression of BCRF1 in *Escherichia coli*

A gene encoding a mature BCRF1 of the sequence given below may be expressed in *E. coli*.

Thr—Asp—Gln—Cys—Asp—Asn—Phe—Pro—Gln—Met—Leu—
Arg—Asp—Leu—Arg—Asp—Ala—Phe—Ser—Arg—Val—Lys—
Thr—Phe—Phe—Gln—Thr—Lys—Asp—Glu—Val—Asp—Asn—
Leu—Leu—Leu—Lys—Glu—Ser—Leu—Leu—Glu—Asp—Phe—
Lys—Gly—Tyr—Leu—Gly—Cys—Gln—Ala—Leu—Ser—Glu—
Met—Ile—Gln—Phe—Tyr—Leu—Glu—Glu—Val—Met—Pro—
Gln—Ala—Glu—Asn—Gln—Asp—Pro—Glu—Ala—Lys—Asp—
His—Val—Asn—Ser—Leu—Gly—Glu—Asn—Leu—Lys—Thr—
Leu—Arg—Leu—Arg—Leu—Arg—Arg—Cys—His—Arg—Phe—
Leu—Pro—Cys—Glu—Asn—Lys—Ser—Lys—Ala—Val—Glu—
Gln—Ile—Lys—Asn—Ala—Phe—Asn—Lys—Leu—Gln—Glu—
Lys—Gly—Ile—Tyr—Lys—Ala—Met—Ser—Glu—Phe—Asp—

-continued

Ile—Phe—Ile—Asn—Tyr—Ile—Glu—Ala—Tyr—Met—Thr—
Ile—Lys—Ala—Arg.

The cDNA insert of pBCRF1(SRα) is recloned into an M13 plasmid where it is altered twice by site-directed mutagenesis: first to form a Cla I site at the 5' end of the coding region for the mature BCRF1 polypeptide, and second to form a Bam HI site at the 3' end of the coding region for the mature BCRF1 polypeptide. The mutated sequence is then readily inserted into the TRPC11 expression vector described below.

The TRPC11 vector was constructed by ligating a synthetic consensus RBS fragment to ClaI linkers (ATGCAT) and by cloning the resulting fragments into ClaI restricted pMT11hc (which had been previously modified to contain the ClaI site). pMT11hc is a small (2.3 kilobase) high copy, $AMP^R$, $TET^S$ derivative of pBR322 that bears the πVX plasmid EcoRI-HindIII polylinker region. (πVX is described by Maniatis et al., Molecular Cloning: A Laboratory Manual, Cold Spring Harbor Laboratory, 1982). This was modified to contain the ClaI site by restricting pMT11hc with EcoRI and BamHI, filling in the 5 resulting sticky ends and ligating with ClaI linker (CATCGATG), thereby restoring the EcoRI and BamHI sites and replacing the SmaI site with a ClaI site. One transformant from the TRPC11 construction had a tandem RBS sequence flanked by ClaI sites. One of the ClaI sites and part of the second copy of the RBS sequence were removed by digesting this plasmid with PstI, treating with Bal31 nuclease, restricting with EcoRI and treating with T4 DNA polymerase in the presence of all four deoxynucleotide triphosphates. The resulting 30–40 bp fragments were recovered via PAGE and cloned into SmaI restricted pUC12. A 248 bp *E. coli* trpP-bearing EcoRI fragment derived from pKC101 (described by Nichols et al. in Methods in Enzymology, Vol. 101, pg. 155 (Academic Press, N.Y. 1983)) was then cloned into the EcoRI site to complete the TRPC11 construction, which is illustrated in FIG. 2. TRPC11 is employed as a vector for BCRF1 by first digesting it with ClaI and Bam HI, purifying it, and then mixing it in a standard ligation solution with the ClaI-Bam HI fragment of the M13 containing the nucleotide sequence coding for the mature BCRF1. The insert-containing TRPC11, referred to as TRPC11-BCRF1, is propagated in *E. coli* K12 strain JM101, e.g. available from the ATCC under accession number 33876.

EXAMPLE 3

Production of BCRF1-Neutralizing Monoclonal Antibody

A male Lewis rat is immunized with purified preparations of COS 7-cell expressed BCRF1. The rat is first immunized with 1 ml of BCRF1 solution (5–100 μg/ml BCRF1 in 10 mM Tris-HCl, 0.5M NaCl, pH 7.4) emulsified with 1 ml Freund's Complete Adjuvant (FCA), and boosted twice with the same amount of material in Freund's Incomplete Adjuvant. Test bleeds are taken. The animal is given a final boost of 25 μg BCRF1 solution in phosphate-buffered saline, and four days later the spleen is obtained for fusion.

Approximately $3 \times 10^8$ rat splenocytes are fused with an equal number of P3X63-AG8.653 mouse myeloma cells (available from the ATCC under accession number CRL 1580) using polyethylene glycol. The cell suspension (approximately $3.5 \times 10^5$ cells/ml in HAT medium) was distributed in to 40 96-well microtiter plates, e.g. following the protocol described in Chretien et al, J. Immunol. Meth., Vol. 117, pgs. 67–81 (1989). Ten days later hybridoma supernatants are tested for their ability to bind BCRF1 immobilized directly on microtiter plates (indirect ELISA), or to BCRF1 bound to immobilized polyclonal IgG fraction of rabbit anti-BCRF1. Bound antibody is detected by peroxidase-conjugated goat anti-rat immunoglobulin with a standard protocol. Hybridomas secreting antibodies reacting with BCRF1 are cloned by limiting dilution. The selected hybridomas are stored (e.g. −70° C. in culture medium with 10% DMSO) and cultured using standard mammalian cell culture techniques (e.g. RPMI 1640 with 10% fetal bovine serum, supplemented with 1 mM glutamine and 50 mM 2-mercaptoethanol). Hybridomas producing BCRF1-blocking antibodies are selected from the set of hybridomas producing BCRF1-specific antibodies by the their ability to counteract the BCRF1-induced suppression of IFN-γ production in the assay described above.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited *E. coli* MC1061 carrying pBCRF1(SRα) with the American Type Culture Collection, Rockville, Md., USA (ATCC), under accession number 68193. This deposit was made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

I claim:

1. An antagonist to BCRF1 wherein the antagonist is capable of blocking BCRF1-induced suppression of interferon-γ, and is a monoclonal antibody or an antigen binding fragment of a monoclonal antibody.

2. The antagonist of claim 1, wherein the monoclonal antibody is capable of recognizing a BCRF1 lacking natural glycosylation.

3. The antagonist of claim 1, wherein the monoclonal antibody is capable of recognizing a biologically-active BCRF1.

4. The antagonist of claim 1, wherein said antagonist is an interspecific monoclonal antibody wherein the binding region of an antibody of a first species is combined with the non-binding region of an antibody of a second species.

5. The antagonist of claim 1, wherein said antagonist is a Fab or a Fv fragment.

6. A cell line capable of making the monoclonal antibody of claim 1.

7. The cell line of claim 6, wherein said cell line has a parental cell from a mouse, rat, rabbit, or human.

8. A pharmaceutical composition comprising the antagonist of claim 1.

9. The pharmaceutical composition of claim 1, further comprising a pharmaceutically acceptable carrier.

10. The pharmaceutical composition of claim 1, wherein the composition is in an implantable drug delivery system.

11. The pharmaceutical composition of claim 1, wherein the composition is in an injectable drug delivery system.

12. The pharmaceutical composition of claim 1, wherein the composition is in a parenteral administration form.

* * * * *